US008003340B2

(12) United States Patent
Kim et al.

(10) Patent No.: US 8,003,340 B2

(45) Date of Patent: Aug. 23, 2011

(54) METHOD AND KIT FOR ISOLATING AND FRACTIONING PHOSPHOPROTEINS

(75) Inventors: Dong Su Kim, Daegu (KR); Hyung Jin Na, Pohang-si (KR); Jae Ho Jang, Busan (KR); Hye-Kyung Kim, Gyeongju-si (KR); Mo Yoel Park, Pohang-si (KR)

(73) Assignees: DCD Inc., Pohang-si, Gyeongsangbuk-do (KR); Genomine, Inc., Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 12/675,758

(22) PCT Filed: Jun. 20, 2008

(86) PCT No.: PCT/KR2008/003515

§ 371 (c)(1), (2), (4) Date: Feb. 26, 2010

(87) PCT Pub. No.: WO2009/028791

PCT Pub. Date: Mar. 5, 2009

(65) Prior Publication Data

US 2010/0233784 A1 Sep. 16, 2010

(30) Foreign Application Priority Data

Aug. 31, 2007 (KR) ........................ 10-2007-0088003

(51) Int. Cl.
*G01N 33/573* (2006.01)
*C07K 1/00* (2006.01)

(52) U.S. Cl. ........................................ 435/7.4; 530/350

(58) Field of Classification Search .................. 435/7.4; 530/350

See application file for complete search history.

(56) References Cited

U.S. PATENT DOCUMENTS

| | | | | |
|---|---|---|---|---|
| 7,102,005 | B2 * | 9/2006 | Agnew et al. | 544/287 |
| 2006/0135407 | A1 | 6/2006 | Silcock et al. | |

OTHER PUBLICATIONS

WIPO, International Search Report for International Application No. PCT/KR2008/003515.

* cited by examiner

*Primary Examiner* — Maryam Monshipouri

(74) *Attorney, Agent, or Firm* — Intellectual Property Law Group LLP; Juneko Jackson

(57) ABSTRACT

Disclosed herein a method and a kit for fractioning/isolating phosphoproteins. Calcium ions, barium ions, cobalt ions and molybdenum ions are bound specifically to phosphoproteins to form metal-phosphoprotein complexes. They can be easily precipitated with precipitants including sulfates, citrates, bicarbonates and carbonates.

18 Claims, 12 Drawing Sheets

1. Ba40AB40SA10sup
2. phosphoprotein fraction of lane 1
3. Ba40AB40SA20sup
4. phosphoprotein fraction of lane 3
5. Ba40SB20SA10sup
6. phosphoprotein fraction of lane 5
7. Ba40SB20SA20sup
8. phosphoprotein fraction of lane 7 yeast extract stained with CBB before the frationation of phosphoproteins yeast extract stained with CBB after the frationation of phosphoproteins phosphoprotein stained after fractioning phosphoproteins staining with CBB phosphoprotein stained with ProQ Diamond total cell lysate fractionated phosphoprotein 1. standard phosphoproteins
2. standard phosphoproteins treated with λPPase
3. proteins remaining after fractioning phosphoproteins of lung cancer tissue
4. phosphoprotein fraction of lung cancer tissue
5. phosphoprotein fraction of lung cancer tissue treated with λPPase phosphoprotein stained with ProQ Diamond staining with CBB

| Protein annotation | Accession | Sequence coverage(%) | pI | MW | Est'd Z |
|---|---|---|---|---|---|
| Component of the TREX complex required for nuclear mRNA export | NP_010199.1 | 18 | 5.3 | 50.63 | 2.07 |

METHOD AND KIT FOR ISOLATING AND FRACTIONING PHOSPHOPROTEINS

CROSS-REFERENCE TO RELATED APPLICATION

This application is a U.S. National Phase application, under 35 U.S.C. §371, of International Application no. PCT/KR2008/003515, with an international filing date of Jun. 20, 2008, which is hereby incorporated by reference for all purposes.

TECHNICAL FIELD

The present invention relates to a method and a kit for isolating and fractioning phosphoproteins.

BACKGROUND ART

It is known that a normal or an abnormal modification of proteins, such as post-translational modification, as well change of protein expression, is implicated in the functional control of genetic information and the abnormal functional change of the body, such as diseases.

Extensive efforts have been made to develop new drugs which control the function of phosphorylation-related enzymes, thereby treating relevant diseases. Representative of such drugs is Gleevec, an anticancer agent.

For designing and developing new drugs for protein phosphorylation-related diseases, the phosphorylated proteins must be isolated and fractioned from cells or tissues in so large an amount as to allow study thereon.

Hence, the present invention aims to provide a method for isolating and fractioning phosphoproteins from cells or tissues.

DISCLOSURE

Technical Problem

Therefore, it is therefore an object to provide a method for effectively fractioning phosphoproteins.

It is another object to provide a method for effectively isolating phosphoproteins.

It is a further object to provide a kit for effectively fractioning phosphoproteins.

It is a still further object to provide a kit for effectively isolating phosphoproteins.

Other or concrete objects will be presented in the following description.

Technical Solution

In an aspect of the present invention, a method for fractioning phosphoproteins is provided.

The method for fractioning phosphoproteins in accordance with the presence invention comprises (a) lysing cells or tissues in a lysis solution to afford a cell or tissue lysate, (b) adding metal ions to the cell or tissue lysate to bind the metal ions with phosphoproteins of the cell or tissue lysate, the metal ions being selected from a group consisting of calcium ions, barium ions, cobalt ions, molybdenum ions, and combinations thereof, (c) precipitating the resulting metal-protein complex with a precipitant selected from a group consisting of sulfate, citrate, bicarbonate and carbonate, and (d) separating the precipitate.

In another aspect, the present invention relates to a method for isolating phosphoproteins. The method comprises (a) lysing cells or tissues in a lysis solution to afford a cell or tissue lysate, (b) adding metal ions to the cell or tissue lysate to bind the metal ions with phosphoproteins of the cell or tissue lysate, the metal ions being selected from a group consisting of calcium ions, barium ions, cobalt ions, molybdenum ions, and combinations thereof, (c) precipitating the resulting metal-protein complex with a precipitant selected from a group consisting of sulfate, citrate, bicarbonate and carbonate, (d) separating the precipitate, and (e) removing the metal ion from the precipitated metal-protein complex.

The method for isolating/fractioning phosphoproteins in accordance with the present invention is characterized by the use of metal ions, such as calcium ion, barium ion, cobalt ion and molybdenum ion, in the capture of phosphoproteins, and by use of salts, such as sulfates, citrates, bicarbonates and/or carbonates, in the precipitation of the metal-protein complex.

That is, phosphoproteins in a cell or tissue lysate are bound to the externally added metal ions and precipitated with the salts, so that they can be isolated and fractioned.

As used herein, the term "cell or tissue" shall mean any cell or tissue that contains phosphoproteins therein. Particularly, the term "cell" has a meaning covering from prokaryotic cells such bacteria to eukaryotic cells such as yeasts, animal cells, plant cells and human cells while the term "tissue" has a meaning covering any tissue isolated from animals, plants or humans. Preferably the term "cell or tissue" means cells or tissues isolated from mammals, especially humans.

As long as it can lyse cells or tissues in a manner suitable for protein isolation/fractionation, any lysis solution may be used in the present invention irrespective of the composition thereof. Those skilled in the art may prepare such a lysis solution within the range of their common ability or may use a commercially available one.

The lysis solution may contain lysozyme, a detergent (e.g., NP-40 (nonyl phenoxylpolyethoxylethanol), TritonX-100 (polyethylene glycol p-(1,1,3,3-tetramethylbutyl)-phenyl ether), CHAPS (3-[(3-cholamidopropy)dimethylammonio]-1-propanesulfonate), etc), and a protein denaturant (DTT (Dithiothreitol), TBP (Tributyl phosphate), urea, thiourea, etc.), and optionally a proteinase inhibitor (benzamidine, AEBSF (4-(2-Aminoethyl)benzenesulfonyl fluoride), Aprotinin, EDTA (ethylenediaminetetraacetic acid), Bestatin, Leupeptin, PMSF (phenylmethanesulphonylfluoride) etc) and/or a phosphatase inhibitor ($Na_3VO_4$, NaF, etc.) in consideration of the fractionation/isolation of phosphoproteins. When the lysis solution is prepared as a buffer, the lysis buffer may contain common buffering ingredients, such as weak alkali/weak acid, a pH modifier (e.g., HEPES (4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), Tris-HCl, ampholyte, PBS, NaCl, etc.) therein as well.

The lysis of cells or tissues may be achieved using a method well known in the art. For example, ultrasonication, use of homogenizer, glass grinder, osmosis, lysozyme, or a detergent (e.g., NP-40, TritonX-100, CHAPS, SDS), iterative freezing and thawing, or a combination thereof may be applied to cell or tissue lysis.

After cell or tissue lysis, it is preferred that the supernatant obtained through centrifugation be used in subsequent processes, with the concomitant removal of insoluble cellular substance, in order to effectively isolate phosphoproteins.

Instead of conducting the step (b) just after the lysis of cells or tissues, a protein denaturation process may be needed prior to the step (b) in order to increase efficiency in the fractionation/isolation of phosphoproteins.

When a protein is phosphorylated, the phosphoric acid group, negatively charged, electrostatically interacts with positively charged amino acid residues to cause a conformational change in the tertiary or quaternary structure of the native protein. In most cases, this conformational change occurs in such a manner that the phosphoric acid group is unexposed to the outside. Thus, when the phosphoprotein is denatured by cleaving the covalent bonds (S—S bond) or non-covalent bonds which contribute to the tertiary or quaternary structure of the protein, the phosphoric group may be exposed to the outside, thereby giving rise to increasing efficiency in the fractionation/isolation of phosphoproteins.

As a rule, protein denaturation is directed toward insolubilization or solubilization. For example, alcohols such as ethanol, acids, many bases, and rennin (an enzyme that catalyzes the coagulation of milk) found in the gastric juice of ruminants are protein denaturants which act to coagulate proteins. On the other hand, DTT, TBP and Tris(carboxyethy)phosphine, which all cleave S—S bonds, or urea, thiourea and detergents such as Triton X-100, CHAPS, NP-40, etc., which all disrupt non-covalent bonds, are denaturants which lead to the formation of solubilizable proteins.

Suitable for use in the present invention are the protein denaturants which make proteins solubilizable as exemplified above. In addition to the examples given above, those skilled in the art may select a proper protein denaturant for use in the present invention from well-known protein denaturants within the range of their common ability.

After the lysis of cells or tissues and optionally the denaturation of proteins, calcium ions, barium ions, cobalt ions and/or molybdenum ions are added to the cell or tissue lysate and thus bind with the phosphoproteins of the cell or tissue lysate.

In a preliminary experiment conducted by the present inventors, various metal ions including the aforementioned metal ions were screened for ability to bind with the standard phosphoproteins, that is, β-casein, α-casein, ovalbumin and pepsin in the same manner as in Example 1, although the results are not shown herein.

The data of the preliminary experiment showed that among the various metal ions screened, only the four metal ions are capable of binding to phosphoproteins, with the highest binding ability detected in calcium ions and barium ions. Therefore, it should be noted that although only calcium ions and barium ions were used in the following Examples, they are not to be construed as the limit of the present invention.

Prior to the binding of the metal ions to phosphoproteins, the compounds or salts which can be dissociated to give negative ions, for example, acetate salts, such as sodium acetate, acetic acids, sodium chloride (NaCl), etc., may be preferably added to the cell or tissue lysate in order to increasing the binding efficiency.

Metal ions, positively charged, generally form a non-specific ionic bond with negatively charged proteins. Thus, the compounds which can bind with calcium ions, barium ions, cobalt ions and/or molybdenum ions, that is, the compounds which can take negative charges, are used as competitive inhibitors to prevent a non-specific bond between proteins and the metal ions such as calcium ions, barium ions, cobalt ions and/or molybdenum ions.

The prevention of the non-specific bond formation between proteins and the metal ions, such as calcium ions, barium ions, cobalt ions and/or molybdenum ions, results in the effective bond formation between the proteins and the metal ions, giving rise to increasing efficiency in the fractionation/isolation of phosphoproteins.

Preferably, salts of acetate, or acetic acid, is used. The reason is that because most of the negative charges of proteins come from carboxyl groups and are associated with positively charged metal ions, acetate or acetic acid, which has a carboxylic group, is more effective as a competitive inhibitor.

Following the binding of calcium ions, barium ions, cobalt ions and/or molybdenum ions to the phosphoproteins of the cell or tissue lysate, the resulting metal-protein complex can be precipitated with salts, such as sulfate, citrate, bicarbonate and/or carbonate.

In another preliminary experiment conducted by the present inventors, various salt compounds were screened for ability to precipitate the metal-phosphoprotein complex in the same manner as in Example 1, although the results are not shown herein. The result of this preliminary experiment showed that among the various salt compounds screened, only the aforementioned salt compounds are capable of precipitating the metal-phosphoprotein complex, with the highest efficiency found in bicarbonate.

Preferably, sodium or ammonium salts of sulfate, citrate, bicarbonate, and carbonate are used as precipitants, with greatest preference for sodium bicarbonate and ammonium bicarbonate.

After the metal-phosphoprotein complex is precipitated with the precipitant, the precipitate may be separated using a well-known method, such as centrifugation.

Following the separation thereof, the precipitated metal-phosphoprotein complex is treated with EDTA or EGTA (ethylene glycol tetraacetic acid) or is subjected to a condition of pH 4.0 or less to remove the metal ions therefrom. Another preliminary experiment in which various chelating agents or conditions were tested demonstrated that only the chelating agents or the pH condition allowed the removal of the metal ions from the metal-phosphoprotein complex.

The phosphoproteins free of metal ions can be isolated as a pure form through fractional precipitation in a suitable solvent, such as distilled water, ethanol, chloroform, acetone, methanol, or a combination thereof.

The method for fractioning/isolating phosphoproteins in accordance with the present invention is found to have a fraction/isolation efficiency of 87% or greater for the standard phosphoproteins and 93% or greater for whole phosphoproteins in comparison to non-phosphoproteins.

Using the method for fractioning/isolating phosphoproteins in accordance with the present invention, the phosphoproteins which are difficult to detect due to the trace amount thereof can be fractioned/isolated at a high concentration. In the following Examples, most of the phosphoproteins of yeast extract were identified through dye visualization in phosphoprotein fractions. Some of them were found to be phosphoproteins as measured by a mass spectrometer.

In accordance with a further aspect thereof, the present invention relates to a kit for fractioning phosphoproteins. The protein-fractioning kit comprises (a) a cell or tissue-lysing solution, (b) metal ions capable of binding to phosphoproteins of a cell or tissue lysate, selected from a group consisting of calcium ions, barium ions, cobalt ions, molybdenum ions and combinations thereof, (c) a precipitant capable of precipitating a metal-phosphoprotein complex, selected from a group consisting of sulfates, citrates, bicarbonates and carbonates, and (d) a means for separating a precipitate.

In accordance with still another aspect thereof, the present invention pertains to a kit for isolating phosphoproteins, comprising (a) a cell or tissue-lysing solution, (b) metal ions capable of binding to phosphoproteins of a cell or tissue lysate, selected from a group consisting of calcium ions, barium ions, cobalt ions, molybdenum ions and combinations thereof, (c) a precipitant capable of precipitating a metal-phosphoprotein complex, selected from a group consisting of sulfates, citrates, bicarbonates and carbonates, (d) a means for separating a precipitate, and (e) a means for removing the metal ion from a metal-phosphoprotein complex.

With regard to meanings and functions of the individual components and interaction between the individual components in the kits for fractioning/isolating phosphoproteins, the foregoing descriptions therefor in the methods for fractioning/isolating phosphoproteins may be applied.

In accordance with still a further aspect thereof, the present invention pertains to a kit for the diagnosis of a phosphoprotein-related disease.

In many diseases, the expression level of phosphoproteins are changed (increased or decreased), resulting from the change of protein kinases in activity or expression level. For example, p53 is a transcription factor, serving as a tumor suppressor which is activated through the phosphorylation thereof upon DNA damage. Once activated, p53 activates the expression of several genes including one encoding for p21, which is known to bind to cyclin dependent kinases (CDK), important for the G1/S transition in the cell cycle, to inhibit their activity, which in turn prevents the phosphorylation of Rb (retinoblastoma), resulting in the suppression of cancer (E. D. Israels at al, The Oncologist, Vol. 5, 6, pp. 510-513, 2000; David Lane. Nature, 414, 1, 2001).

The overexpression of PKB (protein kinase B) is found in various cancers including ovarian cancer, pancreatic cancer, etc. (Cheng, J. Q. et al., Proc. Natl. Acad. Sci. U.S.A., 89, pp. 9267-9271, 1992; Cheng, J. Q. et al., Proc. Natl. Acad. Sci. U.S.A., 93, pp. 3636-3641, 1996), PKCK-2' is known to be involved in suppressing the anticancer agent-induced cell death of cancer (Kim, K. H et al., EMBO JOURNAL, 24, pp.: 3532-3542, 2005).

EGF (Epidermal Growth Factor) receptor tyrosine kinase is involved in the cancer of the epithelial tissues, such as lung cancer, breast cancers, etc. (Morin, M. Oncogene, 19, pp 6574-6583, 2000), ROCK (Rho-associated, coiled-coil-containing protein kinase) is related with various diseases including hypertension, impotence, glaucoma, inflammation, arteriosclerosis, immune suppression, restenosis, asthma, cardiomegaly, etc. (Ishizaki, T. et al., EMBO J., 15, pp. 1885-1893, 1996; Chitaley, et al., Curr. Hypertens. Rep. 2001 Apr., 3 (2), pp. 139-144; Uehata, M. et al., Nature, 389, pp. 990-994, 1997, Chitaley, K. et al., Nature Medicine, 7, pp. 119-122, 2001; Uchida, S. et al., Biochem. Biophys. Res. Commun., 269 (2), pp. 633-40, 2000; Bito, H. et al., Neuron, 26, pp. 431-441, 2000; Takamura, M. et al., Hepatology, 33, pp. 577-581, 2001; Genda, T. et al., Hepatology, 30, pp. 1027-1036, 1999; Rao, et al., Invest. Opthalmol. Vis. Sci., 42, pp. 1029-37, 2001; Ishizuka, T. et al., J. Immunol., 167, pp. 2298-2304, 2001; (Smim okawa, et al., Arterioscler. Thromb. Vasc. Biol., 11, pp. 2351-2358, 2000; Lou, Z. et al., J. Immunol., 167, pp. 5749-5757, 2001; Seaholtz, et al., Circ. Res., 84, pp. 1186-1193, 1999; Yoshii, et al., Am. J. Respir. Cell Mol. Biol., 20, pp. 1190-1200, 1999; Kuwahara, K. et al., FEBS Lett., 452, pp. 314-318, 1999).

Therefore, phosphoprotein expression level-associated diseases can be diagnosed by qualitatively and quantitatively comparing the expression level of phosphoproteins between normal and pathologically affected cells/tissues.

Indeed, higher expression levels of phosphoproteins were apparently detected in lung cancer cell lines, lung cancer tissues, kidney cancer tissues and ovarian cancer tissues than in normal cells/tissues as demonstrated in the following Examples.

The kit for the diagnosis of a phosphoprotein-related disease in accordance with the present invention comprises a) a cell or tissue-lysing solution, (b) metal ions capable of binding to a phosphoprotein of a cell or tissue lysate, selected from a group consisting of calcium ions, barium ions, cobalt ions, molybdenum ions and combinations thereof, (c) a precipitant capable of precipitating a metal-phosphoprotein complex, selected from a group consisting of sulfates, citrates, bicarbonates and carbonates, (d) a means for separating a precipitate, (e) a means for removing the metal ion from a metal-phosphoprotein complex, and (f) a means for qualitatively and quantitatively identifying the phosphoprotein.

With regard to the components (a) to (e) in the diagnostic kit of the present invention, the foregoing descriptions therefor are applied as they are.

As to the component (f) in the diagnostic kit, it may be preferably a staining reagent specific for the phosphoproteins. The staining reagent may be prepared by the user or may be a commercially available one. In the latter case, as used in the following Example, ProQ Diamond Phosphoprotein Gel Stain (Invitrogen) and GelCode Phosphoprotein detection kit (Pierce) may be suitable for use in the present invention.

The diagnostic kit of the present invention may further include instructions that teach how to determine a disease from the qualitative and quantitative identification data for phosphoproteins, thereby allowing the user to determine a disease without depending on a medical expert.

The diagnostic kit of the present invention may be applied to mammals including humans.

Advantageous Effects

According to the present invention, as described, a method and a kit are provided for effectively fractioning/isolating phosphoproteins. Also, the present invention provides a kit for diagnosing a phosphoprotein-related disease.

DESCRIPTION OF DRAWINGS

In FIG. 1, “Ca” stands for $CaCl_2$, “Ba” for $BaCl_2$, “AB” for ammonium bicarbonate, “SB” for sodium bicarbonate, “SA” for sodium acetate and “sup” for supernatant, and numerals given thereto represent the final concentrations (mM) thereof.

In FIGS. 2 to 4, “Ba” stands for $BaCl_2$, “AB” for ammonium bicarbonate, “SB” for sodium bicarbonate, “SA” for sodium acetate, and “sup” for supernatant, and numerals given thereto represent the final concentrations (mM) thereof.

FIG. 5 is an electrophoretogram after phosphoproteins fractioned/isolated in various conditions (lanes 8~14) and the corresponding non-phosphoproteins are electrophoresed and stained with CBB and a dye specific for phosphoproteins.

FIG. 6 provides photographs showing the distribution of pre-fraction yeast extracts and post-fraction phosphoproteins after two-dimensional electrophoresis and straining with CBB and a dye specific for phosphoproteins. In FIG. 5, "Ba" stands for $BaCl_2$, "AB" for ammonium bicarbonate, "sup" for supernatant, and numerals given thereto represent the final concentrations (mM) thereof.

BEST MODE

A better understanding of the present invention may be obtained through the following examples which are set forth to illustrate, but are not to be construed as the limit of the present invention.

Example 1

Fractionation of Standard Phosphoproteins

Calcium ions or barium ions were used as metal ions. Ammonium bicarbonate or sodium bicarbonate served as a precipitant.

The standard phosphoproteins to be fractioned included β-casein, α-casein, ovalbumin, and pepsin. Bovine serum albumin (BSA), a non-phosphoprotein, was used as a control. Each of the standard phosphoproteins and BSA was dissolved at a concentration of 0.025 mg/ml in 1 ml of a urea solution (8M urea, 50 mM Tris-HCl pH 7.5). To this solution was added 10 μl or 20 μl of a 1M sodium acetate solution to give a final concentration of 10 mM or 20 mM. To this protein solution was added 40 μl or 80 μl of 1 M calcium ions (1 M $CaCl_2$) or 1 M barium ions (1 M $BaCl_2$) to dilute the metal ions to a concentration of 40 mM, followed by vortexing for 20 min. Subsequently, the addition of ammonium bicarbonate or sodium bicarbonate induced the precipitation of the metal-phosphoprotein complexes thus formed. In greater detail, 20 μl or 40 μl of 1 M ammonium bicarbonate or 1 M sodium bicarbonate was added to yield a final concentration of 20 mM or 40 mM and mixed for 20 min with vortexing, to induce precipitation. The precipitates thus formed were separated by centrifugation at 12,000×g. In order to remove the metal ions and the precipitant from the precipitates, 0.25 M EDTA was added to the precipitates and stirred until the precipitates were converted to a semi-transparent solution. This solution was mixed with 550 μl of ethanol and 150 μl of chloroform with vortexing for 5 min. 500 μl of distilled water was also added, vortexed for 5 min, and centrifuged at 12,000×g for 5 min. The protein precipitate thus formed in the middle layer was recovered, washed twice with 1 ml of ethanol, and dried in air to afford a phosphoprotein fraction.

Figure 1:
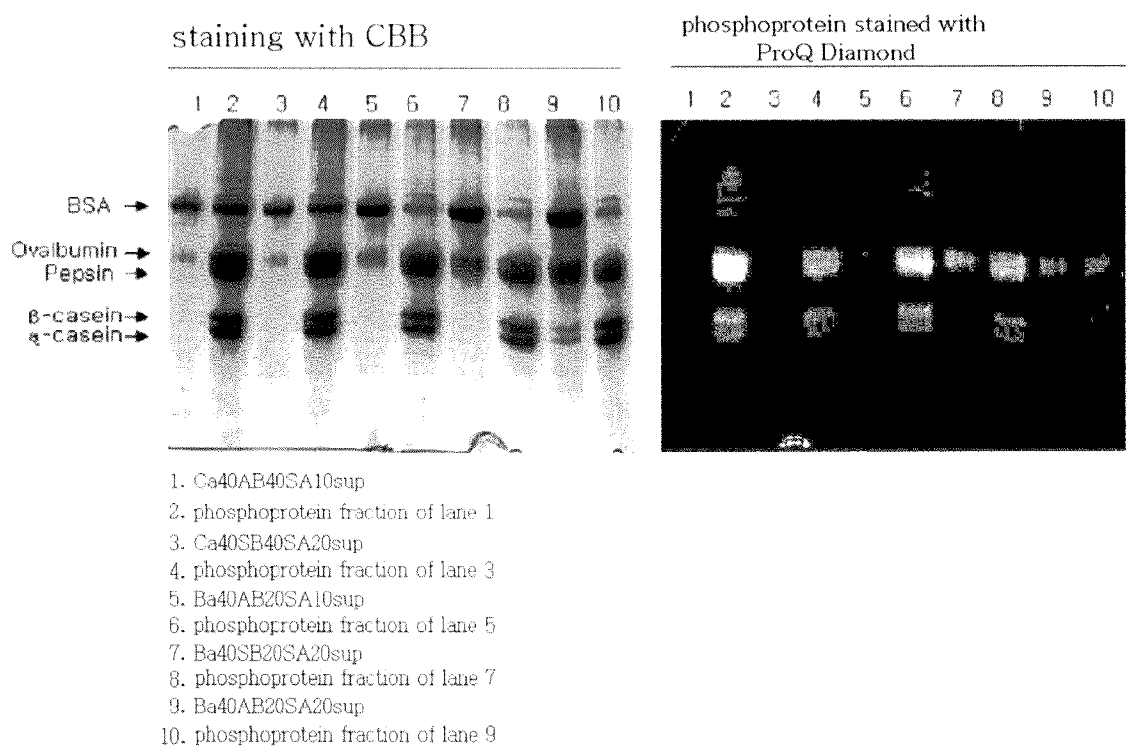
FIG. 1 provides photographs showing the fractionation/isolation results of standard phosphoproteins using metal ions and precipitants at various concentrations, with the non-phosphoprotein BSA serving as a control.

The supernatant and the phosphoprotein fraction were dissolved in SDS-PAGE buffer (Sigma), loaded on an SDS-PAGE kit (Hoeffer), run for 90 min in the presence of an electric field of 120 V, and stained with CBB (Sigma), a general dye for electrophoresis, or with ProQ Diamond (Invitrogen), specific for phosphoproteins, according to the protocol provided by the manufacturer. The electrophoresis pattern obtained is shown in FIG. 1. After the staining, fluorescence was detected for 4 sec within the fluorescent wavelength range of Cy3 and imaged using Diversity (SYNGENE) to visualize phosphoproteins.

With reference to FIG. 1, the standard phosphoproteins used in this experiment are detected in the phosphoprotein fraction.

Example 2

Assay for Fractionation of Phosphoproteins

Ability to fraction phosphoproteins was evaluated in terms of specificity and selectivity for phosphoproteins and yield of phosphoproteins. For this, fractionation was performed on the standard phosphoproteins. In this regard, as described in Example 1, barium ions were used as metal ions, ammonium bicarbonate or sodium bicarbonate was used as a precipitant, and sodium acetate was used as a competitive inhibitor to prevent or eliminate the non-specific binding of the metal ions to phosphoproteins. An experimental process was conducted in a manner similar to that of Example 1.

Figure 2:
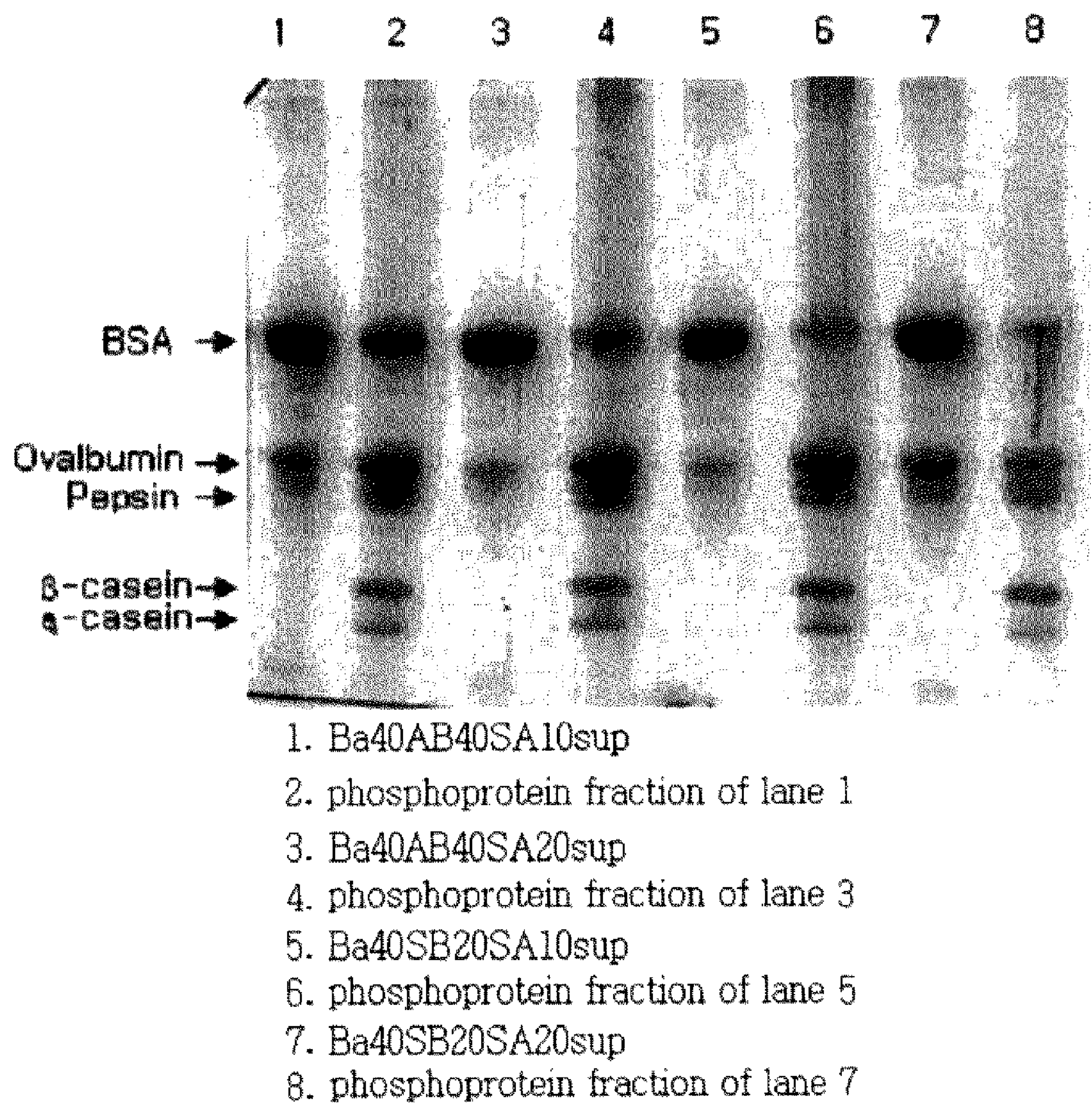
FIGS. 2 to 4 are photographs showing the ability of barium ions and precipitants to fraction phosphoproteins from a mixture of non-phosphoprotein and phosphoproteins.

In greater detail, β-casein, α-casein, ovalbumin and pepsin were used as standard phosphoproteins while bovine serum albumin (BSA), known as a non-phosphoprotein, was used as a control. Each of the standard phosphoproteins and BSA was dissolved at a concentration of 0.025 mg/ml in 1 ml of a urea solution (8M urea, 50 mM Tris-HCl pH 7.5). To this solution was added 10 μl or 20 μl of a 1 M sodium acetate solution to give a final concentration of 10 mM or 20 mM. To this protein solution was added 40 μl of 1 M barium ions (1 M $BaCl_2$) to dilute the metal ions to a concentration of 40 mM, followed by vortexing for 20 min. Subsequently, 20 μl of 1 M ammonium bicarbonate or sodium bicarbonate was added to yield a final concentration of 20 mM and mixed for 20 min with vortexing, to induce precipitation. The precipitates thus formed were separated by centrifugation at 12,000×g, and treated in the same manner as in Example 1 to remove the metal ions and the precipitant therefrom. The supernatant and the phosphoprotein fractions thus obtained were dissolved in SDS-PAGE buffer (Sigma), loaded on an SDS-PAGE kit (Hoeffer), run for 90 min in the presence of an electric field of 120 V, and stained with CBB (Sigma), a general dye for electrophoresis. The electrophoresis pattern obtained is shown in FIG. 2. After the staining, fluorescence was detected and imaged in the same manner as in Example 1 to visualize the stained proteins.

Figure 3:
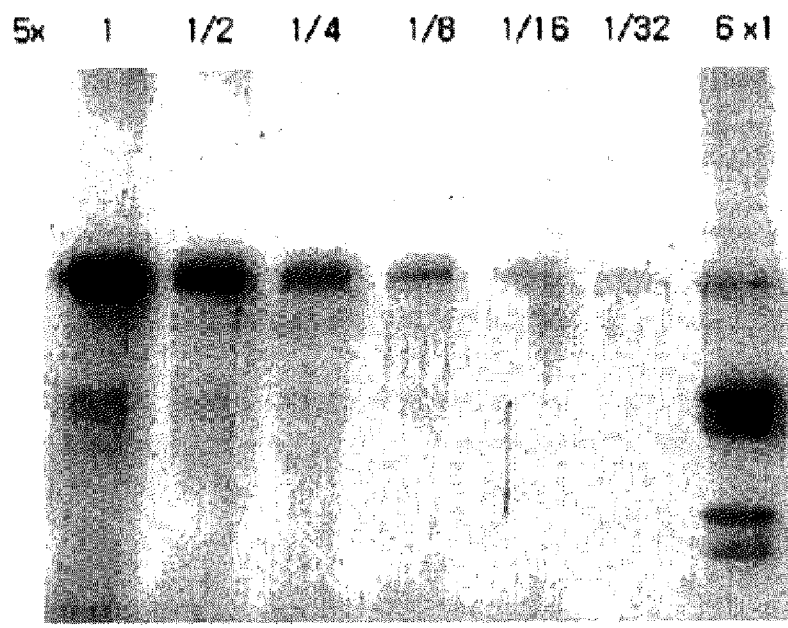
Figure 4:
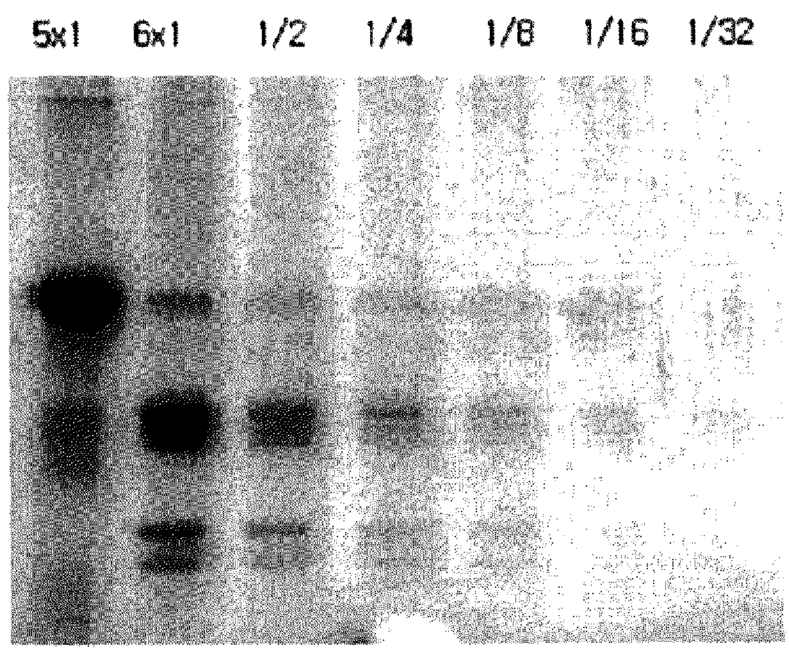

Fraction 5 was serially diluted with distilled water, and electrophoresed. The electrophoresis results are shown in FIG. 3 along with Fraction 6. Likewise, Fraction 6 was serially diluted with distilled water, followed by electrophoresis, and the electrophoresis results are shown in FIG. 4 along with Fraction 5.

In FIG. 2, the lanes of the precipitates, that is, the phosphoprotein fractions are apparently observed to contain the standard phosphoproteins used. The electrophoretogram of FIG. 3 shows that the amount of BSA in Fraction 6 is about 1/16 of that of BSA in Fraction 5. As can be inferred from the data of FIG. 4, the level of the phosphoproteins in Fraction 6 is about 8 to 32 times greater than that of the phosphoproteins in Fraction 5.

Example 3

Fractionation of Phosphoprotein from Yeast Extract 600 mg of yeast cells (Saccharomyces cerevisiae) which had been stored in a deep freezer (−80° C.) was suspended in 1 ml of a protein extraction buffer for two-dimensional electrophoresis (7 M urea, 2 M Thiourea, 4% (w/v) 3-[(3-cholamidopropy)dimethylammonio]-1-propanesulfonate (CHAPS), 1% (w/v) dithiothreitol (DTT), 2% (v/v) pharmalyte, 1 mM benzamidine) and disrupted by ultrasonication with 4 cycles of 30 sec in an ultrasonicator (HD2200, BANDELIN SONOPULSE). The yeast cell lysate thus formed was centrifuged at 12,000×g for 30 min to remove insoluble substance therefrom and the supernatant was used for protein fractionation. The protein solution was added to 1 ml of urea buffer (8 M urea, 50 mM Tris-HCl pH 7.5) to give a final protein concentration of 0.5 mg/ml. To this protein solution was added 80 μl of 1 M barium ions (1 M $BaCl_2$) to dilute the metal ions to a concentration of 80 mM, followed by vortexing for 20 min. Subsequently, 60 μl or 80 μl of 1 M ammonium bicarbonate was added to yield a final concentration of 60 mM or 80 mM and mixed for 20 min with vortexing, to induce precipitation. The precipitates thus formed were separated by centrifugation at 12,000×g, and treated in the same manner as in Example 1 to remove the metal ions and the precipitant therefrom. The supernatant and the phosphoprotein fractions thus obtained were dissolved in SDS-PAGE buffer (Sigma), loaded on an SDS-PAGE kit (Hoeffer), run for 90 min in the presence of an electric field of 120 V, and stained with CBB (Sigma), a general dye for electrophoresis, or with ProQ Diamond (Invitrogen). After the staining, fluorescence was detected and imaged in the same manner as in Example 1 to visualize the stained proteins.

Figure 5:
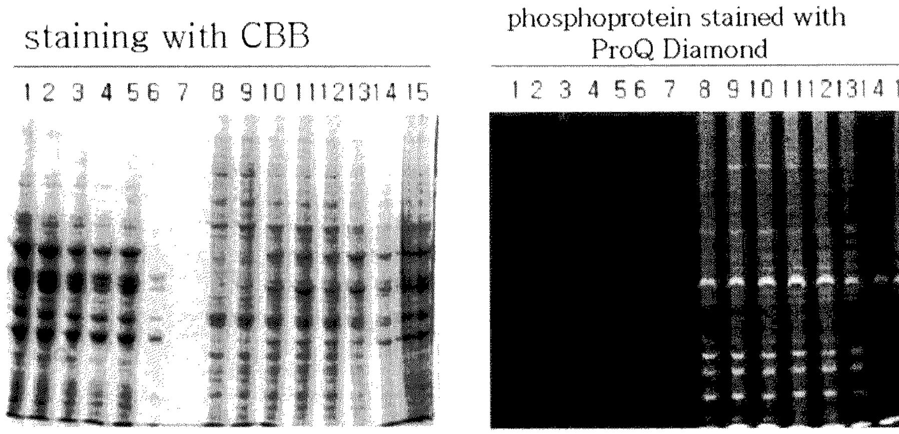
FIGS. 5 and 6 are photographs the assay results of fractioning/isolating phosphoproteins from a yeast extract.

The electrophoresis pattern obtained is shown in FIG. 5. As seen in this electrophoretogram, the phosphoproteins were properly fractioned.

Two-dimensional electrophoresis was performed with pre-fraction total proteins (the total yeast protein obtained after the removal of insoluble substance from the disrupted yeast extract by centrifugation at 12,000×g for 30 min) and post-fraction phosphoproteins.

First, the pre-fraction total proteins and the post-fraction phosphoproteins were dissolved in 120 μl of respective protein extraction buffer for two-dimensional electrophoresis (7 M urea, 2 M Thiourea, 4% (w/v) 3-[(3-cholamidopropy)dimethylammonio]-1-propanesulfonate (CHAPS), 1% (w/v) dithiothreitol (DTT), 2% (v/v) pharmalyte, 1 mM benzamidine). For isoelectric focusing (IEF), IPG strips were rehydrated at room temperature for 12-16 hours in a reswelling tray containing a rehydration buffer composed of 7 M urea, 2 M thiourea, 2% 3-[(3-cholamidopropy)dimethylammonio]-1-propanesulfonate (CHAPS), 1% dithiothreitol (DTT) and 1% pharmalyte. The strips were 8.5 cm strips (pH4~10) manufactured in an IPG type by Genomine, Inc (Pohang, Korea). Samples were weighed 300 g per strip and IEF was performed at using a Multiphore II system (Amersham Biosciences) according to the protocol provided by the manufacturer. For IEF, the voltage was linearly increased from 150 to 3500 V over 3 hours for sample entry, then the voltage was held constant at 3500 V for 12 hours with the focusing complete after 96 kVh.

Prior to the second dimension SDS-PAGE, the IPG strips were incubated for 10 min in equilibration buffer (50 mM Tris-Cl, pH 6.8 containing 6 M urea, 2% SDS and 30% glycerol) first with 1% DTT and second with 2.5% iodoacetamide. Each equilibrated strip was then put onto a SDS-PAGE gel (20×24 cm 10-16% gel concentration gradient), and the second dimension was run at 20° C. in a Hoeffer DALT 2D system (Amersham Biosciences), with the focusing complete after 1.7 kVh.

The gel was stained with CBB, a general dye for electrophoresis, or with ProQ Diamond (Invitrogen), specific for phosphoproteins, according to the protocol provided by the manufacturer. After the staining, fluorescence was detected and imaged in the same manner as in Example 1 to visualize the stained proteins.

Figure 6:
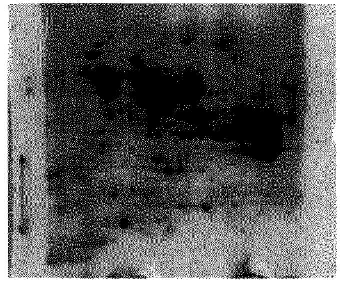
Figure 6:
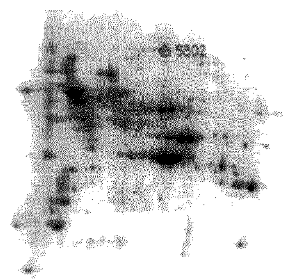
Figure 6:
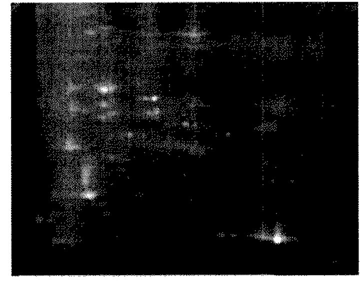

The results are shown in FIG. 6.

Referring to FIG. 6, phosphoproteins are observed to be properly fractioned.

Example 4

Fractionation of Phosphoproteins from Lung Cancer Cell Line 300 mg of the lung cancer cell line (h460) which had been stored at a deep freezer (−80° C.) was suspended in 1 ml of a protein extraction buffer for two-dimensional electrophoresis (7 M urea, 2 M Thiourea, 4% (w/v) 3-[(3-cholamidopropy)dimethylammonio]-1-propanesulfonate (CHAPS), 1% (w/v) dithiothreitol (DTT), 2% (v/v) pharmalyte, 1 mM benzamidine) and disrupted by ultrasonication with 3 cycles of 30 sec in an ultrasonicator (HD2200, BANDELIN SONOPULSE). The lung cancer cell lysate thus formed was centrifuged at 12,000×g for 30 min to remove insoluble substance therefrom and the supernatant was used for protein fractionation. The protein solution was diluted with an 8 M urea solution to give 3 ml of a protein solution with a final protein concentration of 1 mg/ml. To this protein solution was added 1 M Tris-HCl pH 7.5 to give a final concentration of 50 mM. Following the addition of 240 μl of 1 M $BaCl_2$, the solution was well mixed with vortexing for 20 min. Subsequently, 360 μl of 1 M ammonium bicarbonate was added and mixed for 20 min with vortexing, to induce precipitation. The precipitates thus formed were separated by centrifugation at 12,000×g, and treated in the same manner as in Example 1 to remove the metal ions and the precipitant therefrom so that the phosphoprotein fractions can be obtained.

The pre-fraction total proteins and the post-fraction phosphoproteins were subjected to two-dimensional electrophoresis in the same manner as in Example 3, followed by visualization. The results are shown in FIG. 7.

Figure 7:
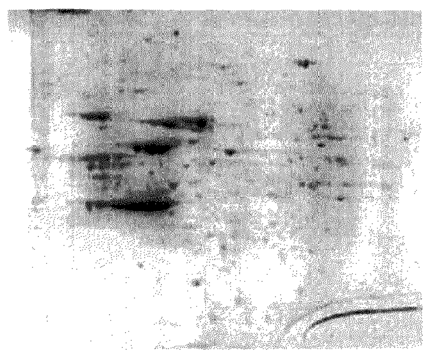
FIG. 7 provides photographs showing the distribution of proteins in a lung cancer cell line upon two-dimensional electrophoresis before and after the fractionation of phosphoproteins from the cell line.
Figure 7:
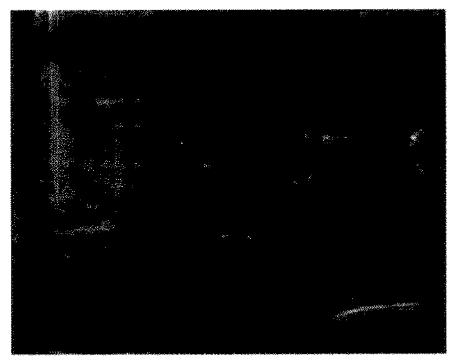
Figure 7:
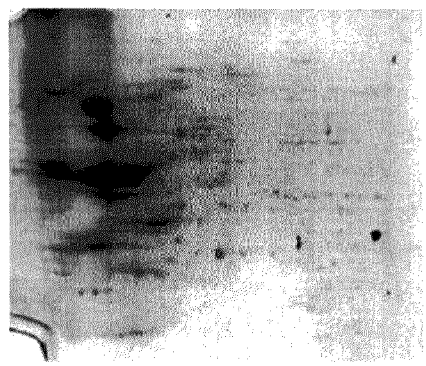

Referring to FIG. 7, phosphoproteins are observed to be properly fractioned.

Example 5

Fractionation of Phosphoproteins from Lung Cancer Tissue 400 mg of a lung cancer tissue which had been stored at a deep freezer (−80° C.) was suspended in 0.5 ml of a protein extraction buffer for two-dimensional electrophoresis (7 M 2 M Thiourea, 4% (w/v) 3-[(3-cholamidopropy)dimethylammonio]-1-propanesulfonate (CHAPS), 1% (w/v) dithiothreitol (DTT), 2% (v/v) pharmalyte, 1 mM benzamidine) and homogenized with an electric homogenizer, followed by cell disruption by ultrasonication with 3 cycles of 30 sec in an ultrasonicator (HD2200, BANDELIN SONOPULSE). The lung cancer tissue extract thus formed was centrifuged at 12,000×g for 30 min to remove insoluble substance therefrom and the supernatant was used for protein fractionation. The protein solution was diluted with an 8 M urea solution to give 3 ml of a protein solution with a final protein concentration of 0.7 mg/ml. To this protein solution was added 1 M Tris-HCl pH 7.5 to give a final concentration of 50 mM. Following the addition of 240 μl of 1 M $BaCl_2$, the solution was well mixed with vortexing for 20 min. Subsequently, 360 μl of 1 M ammonium bicarbonate was added and mixed for 20 min with vortexing, to induce precipitation. The precipitates thus formed were separated by centrifugation at 12,000×g, and treated in the same manner as in Example 1 to remove the metal ions and the precipitant therefrom so that the phosphoprotein fractions can be obtained.

The pre-fraction total proteins and the post-fraction phosphoproteins were subjected to two-dimensional electrophoresis in the same manner as in Example 3, followed by visualization. The results are shown in FIG. 8.

Figure 8:
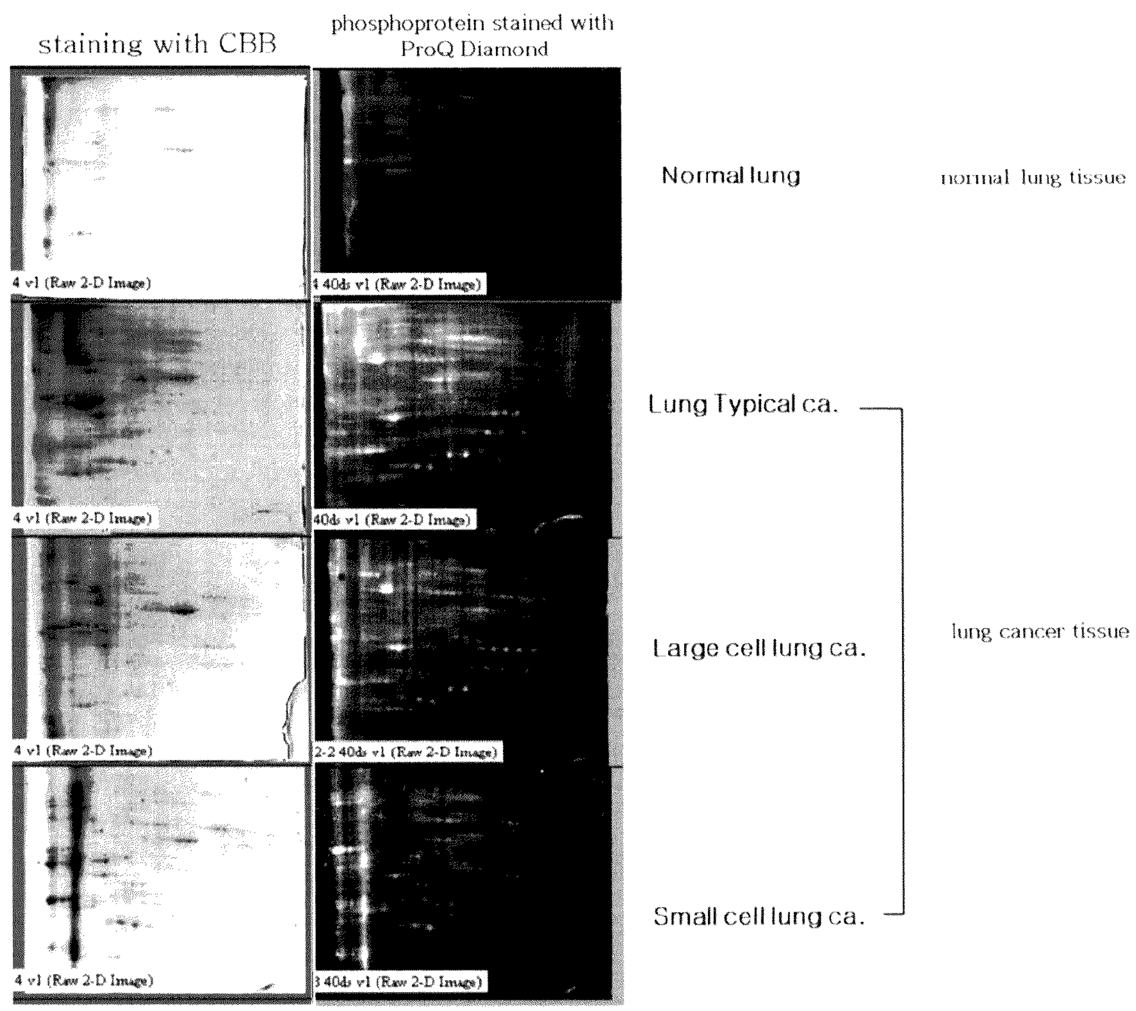
FIG. 8 provides photographs showing the distribution of phosphoproteins fractioned/isolated from a human normal lung tissue and a human lung cancer tissue upon two-dimensional electrophoresis.

Referring to FIG. 8, more proteins were observed to be phosphorylated in lung cancer tissues than in a normal lung tissue, indicating that phosphorylation occurs in different patterns between normal tissues and cancer tissues.

Example 6

Fractionation of Phosphoproteins from Kidney Cancer Tissue 400 mg of each of the normal kidney tissue and the kidney cancer tissue which had been stored in a deep freezer (−80° C.) was fractioned, subjected to two-dimensional electrophoresis and imaged in the same manner as in Example 5. The results are shown in FIG. 9.

Figure 9:
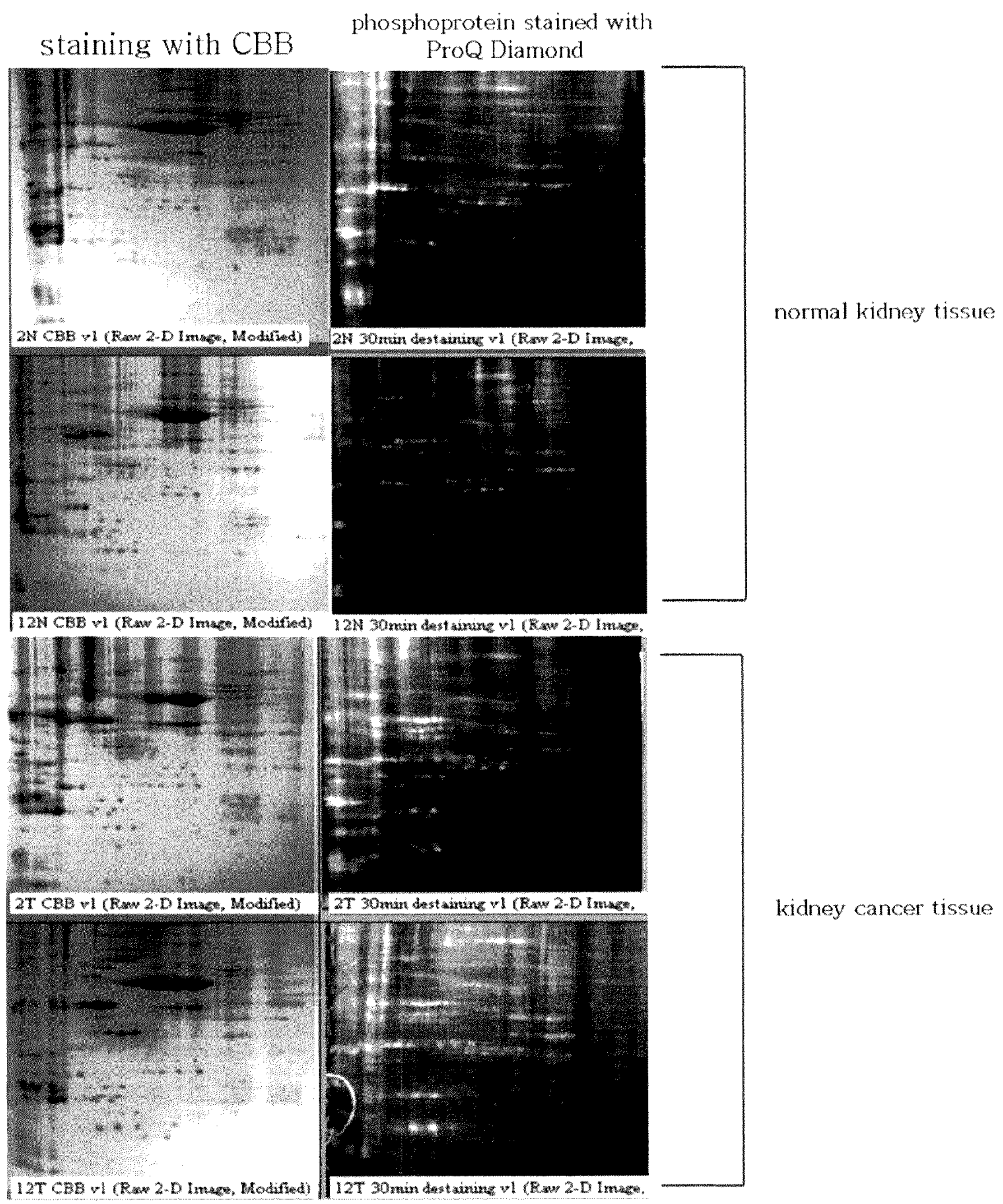
FIG. 9 provides photographs showing the distribution of phosphoproteins fractioned/isolated from a human normal kidney tissue and a human kidney cancer tissue upon two-dimensional electrophoresis.

With reference to FIG. 9, greater protein phosphorylation, as similar to the pattern of FIG. 8, is found in the kidney cancer tissue than in the normal kidney tissue.

Example 7

Fractionation of Phosphoproteins from Ovarian Cancer Tissue 400 mg of each of the normal ovarian tissue and the ovarian cancer tissue which had been stored in a deep freezer (−80° C.) was fractioned, subjected to two-dimensional electrophoresis and imaged in the same manner as in Example 5. The results are shown in FIG. 10.

Figure 10:
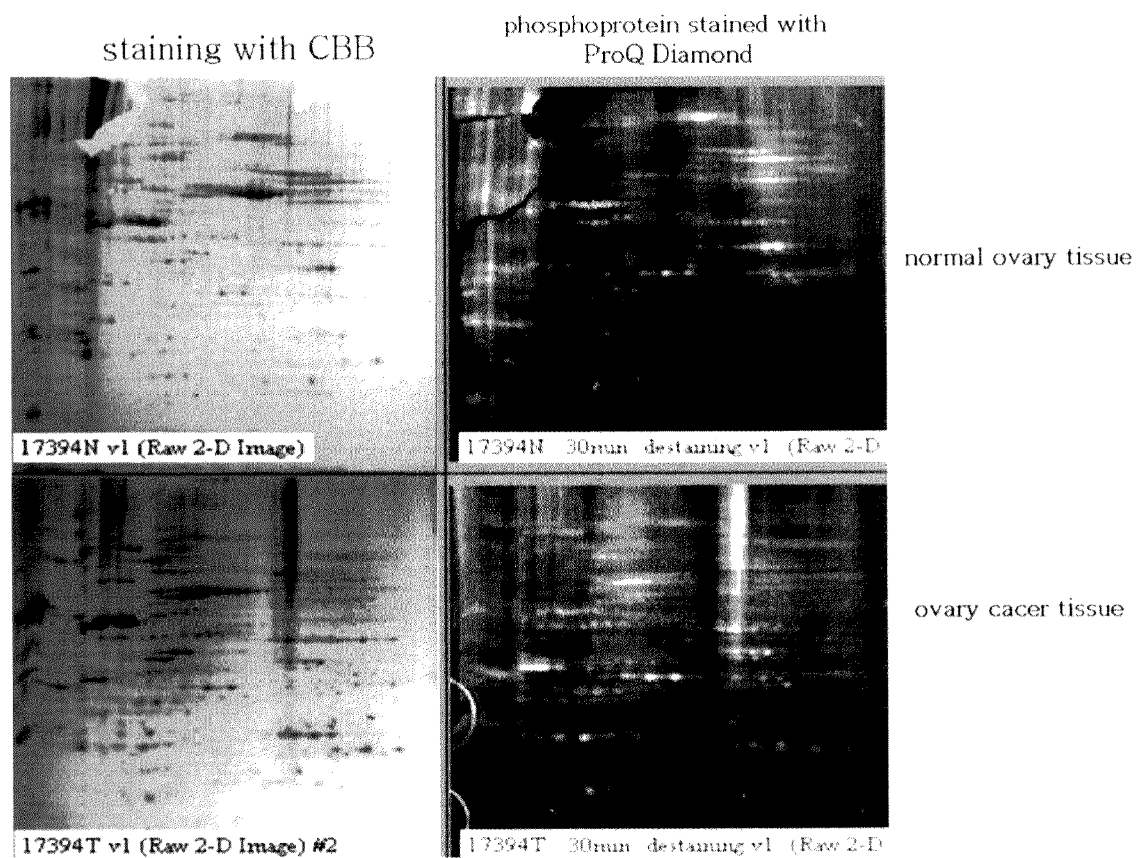
FIG. 10 provides photographs showing the distribution of phosphoproteins fractioned/isolated from a human normal ovary tissue and a human ovary cancer tissue upon two-dimensional electrophoresis.

With reference to FIG. 10, greater protein phosphorylation, as similar to the pattern of FIG. 8, is found in the ovarian cancer tissue than in the normal ovarian tissue.

Example 8

Dephosphorylation of Phosphoprotein Fraction from Lung Cancer Tissue

In order to determine whether the separated protein fraction was a phosphorylation fraction, the following experiment was conducted in such a manner that the protein fraction was treated with λPPase, a dephosphorylation enzyme, followed by phosphoprotein-specific staining.

Figure 11:
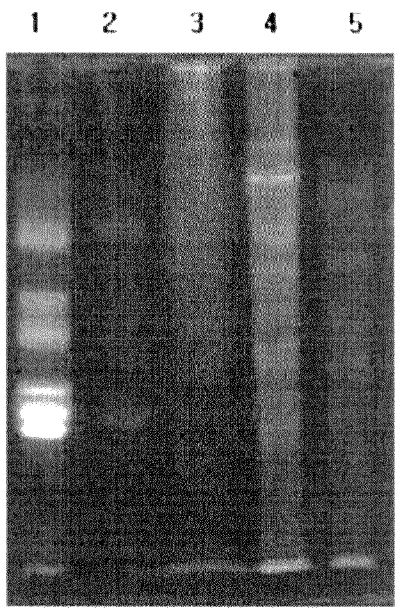
FIG. 11 provides photographs showing that after being treated with a dephosphorylase, the fractioned phosphoproteins are not stained with a dye (ProQ Diamond) specific for phosphoproteins, identifying the fractioned protein as phosphoproteins.
Figure 11:
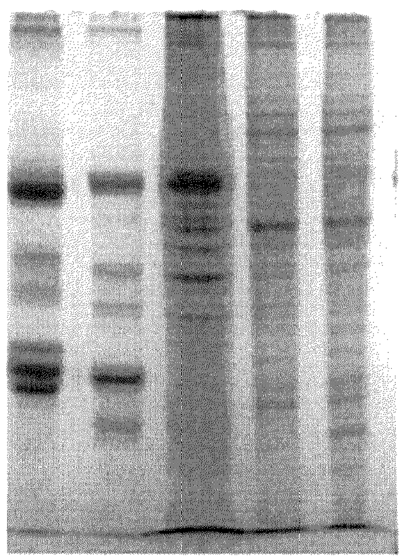

10 μl of the lung phosphoprotein solution used for two-dimensional electrophoresis in Example 5 was 10-fold diluted in 0.1% SDS buffer. A 10× reaction buffer was added in a one-tenth volume to afford a solution containing 50 mM Tris-HCl pH7.5, 0.1 mM EDTA, 5 mM DTT and 0.01% BRIJ 35, for optimal reaction condition for λPPase. To this were added 20 units of λPPase, and then the solution was treated with $MnCl_2$ at a final concentration of 0.1 mM. This solution was incubated overnight at 30° C. to induce dephosphorylation. The reactant mixture was subjected to SDS-PAGE, followed by ProQ Diamond staining as in Example 1. The result images are given in FIG. 11.

As is apparent from the electrophoretogram, the fraction obtained in Example 5 was a phosphoprotein fraction.

Example 9

Protein Fingerprinting of Yeast-Derived Phosphoprotein Spots and Identification of Phosphoprotein 9-1. Protein Fingerprinting of Yeast-Derived Phosphoprotein Spots Protein Spot 3405 of Example 3 (see FIG. 6) was enzymatically digested into smaller fragments by modified porcine trypsin according to the method of Shevchenko et al. (Anal. chem. 1996, 68:850-858) as follows.

First, Protein Spot 3405 was excised from the gel. It was washed with 50% aceonitrile to remove SDS, organic solvents, dye and other impurities therefrom. To the excised gel piece was added a protein digestion solution ((trypsin 8-10 ng/μl, trypsin digestion buffer: ACN 5%, $NH_4HCO_3$ 5%, DW 90%) 5 μl/spot), followed by rehydration at 37° C. for 8-10 hours. The addition of 5 μl of 0.5% trifluoroacetic acid terminated the protein digestion. The protein fragments resulting from trypsin digestion were collected as an aqueous solution which was then desalted and concentrated into 1~5 μl using C18ZipTips (Millipore, USA). This concentrate was mixed with one volume of a matrix solution (α-cyano-4-hydroxycinnamic acid saturated in 50% aqueous acetonitrile) and used for mass analysis. In this regard, protein analysis was performed using Ettan MALDI-TOF (Amersham Biosciences). Protein fragments loaded on target plates were evaporated with an N2 laser at 337 nm and accelerated with a 20 Kv injection pulse to analyze the time of flight. Each mass spectrum for protein spots was the cumulative average of 300 laser shots. The spectra were calibrated with the trypsin autodigestion ion peaks m/z (842.510, 2211.1046) as internal standards. The search program ProFound, developed by Rockefeller University (129.85.19.192/profound bin/WebProFound.exe), was used for protein identification using peptide mass fingerprinting.

Figure 12:
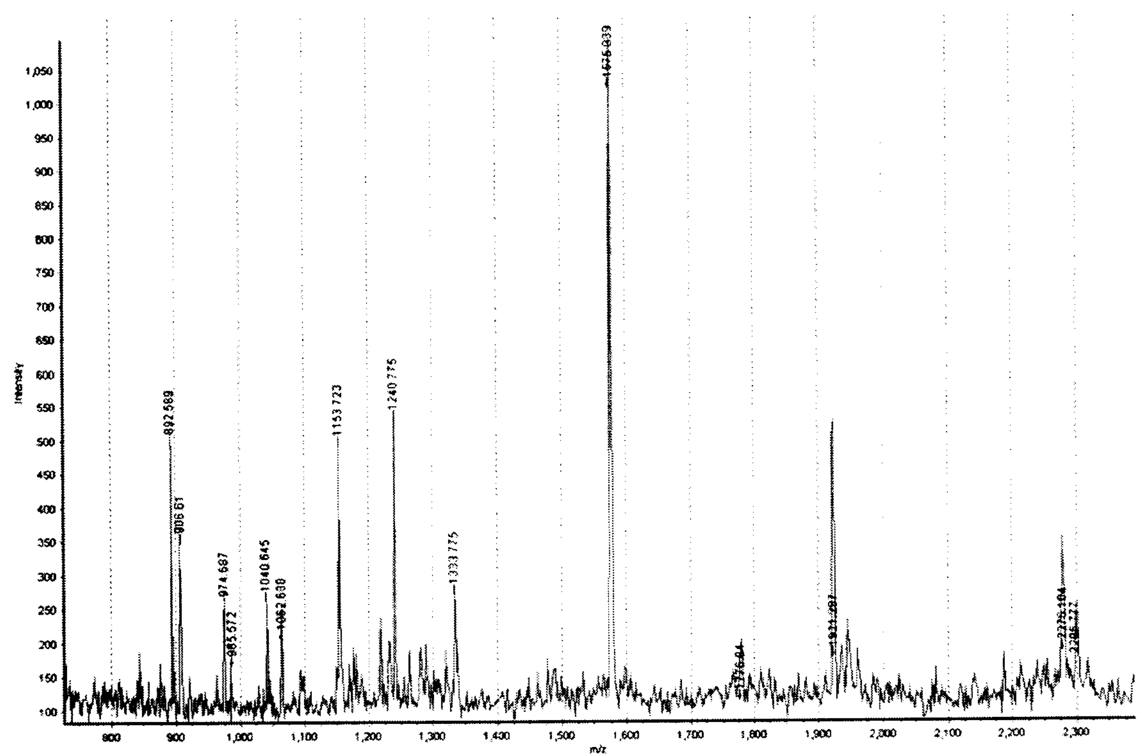
FIGS. 12 and 13A-B are spectra of the protein spots fractioned/isolated from a yeast extract and stained with phosphoprotein-specific dye, measured by a mass spectrometer.

As shown in FIG. 12, the protein spot was identified as GenBank Accession No. NP-010199.1.

9-2. Identification of Phosphoprotein

The protein fragments obtained in Example 9-1, that is, phosphopeptides were concentrated in 1.5 ml or 0.5 ml micro-centrifuge tubes using the phosphopeptide enrichment kit Phos-Pep™ (Genomine, Korea). 10 μl of the peptide mixture of the phosphoprotein was mixed with 5 μl of the main reagent (A solution) of Phos-Pep™, vortexed for several sec, and incubated at room temperature for 5 min. Subsequently, it was mixed with 5 μl of the sub-reagent (B solution), vortexed for several seconds and incubated at room temperature for 20~30 min. At this time, precipitates were formed in a suspension state. During this time period, the precipitates were changed into transparent crystals while being deposited on the wall of the tubes or existing as particulates. The precipitates were washed by adding 50~100 μl of 250 mM ammonium acetate and vortexing for several sec. The washing solution was pipetted out.

The concentrated phosphopeptide precipitate was dissolved in 10 μl of a 1% phosphoric acid solution, desalted, and concentrated into 1~5 μl using C18ZipTips (Millipore). This concentrate was mixed with one volume of α-cyano-4-hydroxycinnamic acid-saturated 50% aqueous acetonitrile and loaded onto target plates for mass analysis. In this regard, protein analysis was performed using Ettan MALDI-TOF (Amersham Biosciences). Protein fragments loaded on the target plates were evaporated with an N2 laser at 337 nm and accelerated with a 20 Kv injection pulse to analyze the time of flight. Mass spectra were recorded in positive reflection mode. Each mass spectrum for protein spots was the cumulative average of 300 laser shots. The spectra were calibrated with the trypsin auto-digestion ion peaks m/z (842.510, 2211.1046) as internal standards.

Figure 13:
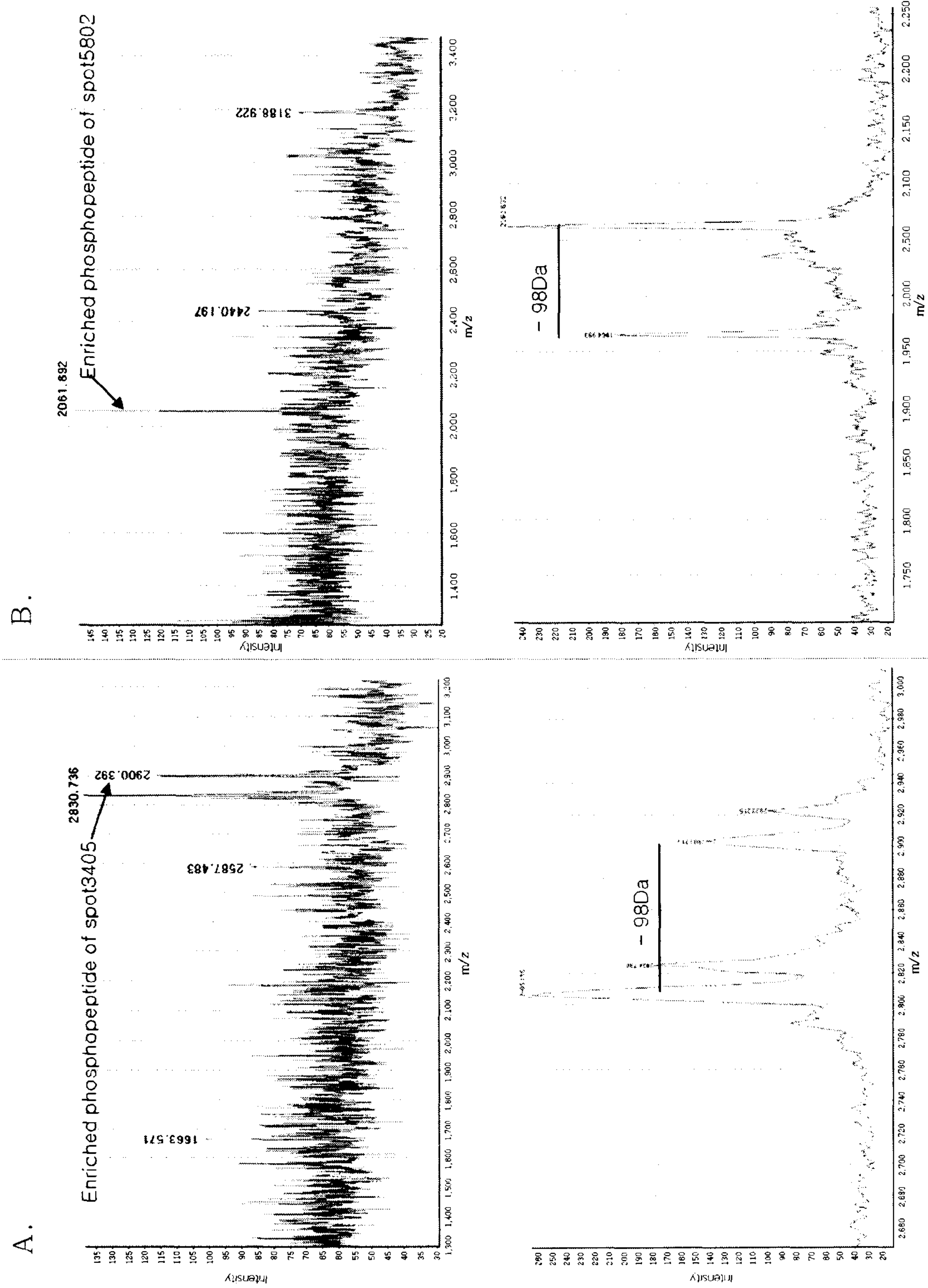

The identification of phosphoproteins containing phosphoserine or phosphothreonine was analyzed from results of the mass spectrometry conducted by MALDI-TOF in the PSD (post source decay) mode, a fragmentation mode, under the condition of low energy source for examining whether a phosphoric acid group is eliminated from a phosphopeptide by β-elimination to form a dephosphorylated peptide with 98 Da or 80 Da in the positive mode. As for the phosphopeptides containing phosphotyrosine residues, their identification is achieved by sequencing them in a chemical assisted fragmentation manner and analyzing the molecular weight of the amino acids in MALDI-TOF PSD mode because the phosphoric acid group is not removed by β-elimination (see FIG. 13A).

On the other hand, the same procedure was applied to the protein spot 5802 (see FIG. 6) to examine the presence of phosphoproteins.

We claim:

1. A method for fractioning phosphoproteins, comprising:

(a) lysing cells or tissues in a lysis solution to afford a cell or tissue lysate;

(b) adding a metal ion to the cell or tissue lysate to bind the metal ion with phosphoproteins of the cell or tissue lysate to form a metal-phosphoprotein complex, the metal ion being selected from a group consisting of calcium ions, barium ions, cobalt ions, molybdenum ions, and combinations thereof;

(c) precipitating the metal-phosphoprotein complex with a precipitant selected from a group consisting of sulfate, citrate, bicarbonate and carbonate, to form a precipitate; and (d) separating the precipitate.

2. The method according to claim 1, wherein the lysis solution is selected from a group consisting of lysozyme, a detergent, a protein denaturant, a protease inhibitor, a phosphatase inhibitor and a combination thereof.

3. The method according to claim 1, further comprising centrifuging the cell or tissue lysate to obtain a supernatant free of insoluble substance, after the step (a).

4. The method according to claim 1, wherein the cell or tissue lysate is treated with a protein denaturant to make proteins solubilized.

5. The method according to claim 4, wherein the protein denaturant is selected from a group consisting of DTT, TBP, Tris(carboxyethy)phosphine, urea, thiourea, NP-40, TritonX-100, CHAPS and a combination thereof.

6. The method according to claim 1, further comprising adding to the cell or tissue lysate a compound or salt which is dissociated to give a negative ion, before or after the step (b).

7. The method according to claim 6, wherein the compound or salt which is dissociated to give a negative ion is selected from acetate salts, acetic acids, and sodium chloride.

8. The method according to claim 1, wherein the precipitant is selected from a group consisting of sodium sulfate, sodium citrate, sodium bicarbonate, sodium carbonate, ammonium sulfate, ammonium citrate, ammonium bicarbonate and ammonium carbonate.

9. The method according to claim 1, further comprising adding EDTA or EGTA to the precipitate or subjecting the precipitate into a condition of pH 4.0 or less to remove the metal ion from the precipitate, after the step (d).

10. A kit for fractioning phosphoproteins, comprising:

(a) lysing cells or tissues in a lysis solution to afford a cell or tissue lysate;

(b) adding a metal ion to the cell or tissue lysate to bind the metal ion with phosphoproteins of the cell or tissue lysate to form a metal-phosphoprotein complex, the metal ion being selected from a group consisting of calcium ions, barium ions, cobalt ions, molybdenum ions, and combinations thereof;

(c) precipitating the metal-phosphoprotein complex with a precipitant selected from a group consisting of sulfate, citrate, bicarbonate and carbonate, to form a precipitate; and (d) a means for separating the precipitate.

11. The kit according to claim 10, wherein the lysis solution is selected from a group consisting of lysozyme, a detergent, a protein denaturant, a protease inhibitor, a phosphatase inhibitor and a combination thereof.

12. The kit according to claim 10, further comprising a means for removing insoluble substance from the cell or tissue lysate through centrifugation.

13. The kit according to claim 10, further comprising a protein denaturant for use in causing proteins to be solubilized.

14. The kit according to claim 13, wherein the protein denaturant is selected from a group consisting of DTT, TBP, Tris(carboxyethy)phosphine, urea, thiourea, NP-40, TritonX-100, CHAPS and a combination thereof.

15. The kit according to claim 10, further comprising a compound or salt which can be dissociated to give a negative ion.

16. The kit according to claim 15, wherein the compound or salt which is dissociated to give a negative ion is selected from among acetate salts, acetic acids, and sodium chloride.

17. The kit according to claim 16, wherein the precipitant is selected from a group consisting of sodium sulfate, sodium citrate, sodium bicarbonate, sodium carbonate, ammonium sulfate, ammonium citrate, ammonium bicarbonate and ammonium carbonate.

18. The kit according to claim 10, further comprising a means for adding EDTA or EGTA to the precipitate or for subjecting the precipitate into a condition of pH 4.0 or less to remove the metal ion from the precipitate.

* * * * *